United States Patent
Bathina et al.

(10) Patent No.: US 9,462,987 B2
(45) Date of Patent: Oct. 11, 2016

(54) DETERMINING PLAQUE DEPOSITS IN BLOOD VESSELS

(71) Applicants: Yogesh Bathina, Bangalore (IN); Parmeet Singh Bhatia, Bangalore (IN); Rajendra Prasad Jadiyappa, Bangalore (IN); Amit Kale, Bangalore (IN)

(72) Inventors: Yogesh Bathina, Bangalore (IN); Parmeet Singh Bhatia, Bangalore (IN); Rajendra Prasad Jadiyappa, Bangalore (IN); Amit Kale, Bangalore (IN)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/560,948

(22) Filed: Dec. 4, 2014

(65) Prior Publication Data

US 2016/0157805 A1 Jun. 9, 2016

(51) Int. Cl.
*G06K 9/00* (2006.01)
*A61B 6/00* (2006.01)
*G06T 5/50* (2006.01)

(52) U.S. Cl.
CPC .............. *A61B 6/5217* (2013.01); *A61B 6/463* (2013.01); *A61B 6/504* (2013.01); *G06T 5/50* (2013.01); *G06T 2207/10116* (2013.01); *G06T 2207/20224* (2013.01); *G06T 2207/30101* (2013.01)

(58) Field of Classification Search
USPC .................................................. 382/128–134
See application file for complete search history.

(56) References Cited

U.S. PATENT DOCUMENTS

| | | | | |
|---|---|---|---|---|
| 5,644,646 A * | 7/1997 | Du | ........................ | G06T 5/008 324/308 |
| 2005/0043614 A1* | 2/2005 | Huizenga | ............... | A61B 5/055 600/427 |
| 2005/0249391 A1* | 11/2005 | Kimmel | ............... | G06T 7/0081 382/128 |
| 2006/0171585 A1* | 8/2006 | Rinck | .................... | A61B 6/504 382/173 |
| 2007/0230653 A1* | 10/2007 | Okamoto | ........... | A61B 5/02007 378/8 |
| 2007/0260141 A1* | 11/2007 | Margolis | ............ | A61B 5/02007 600/437 |
| 2011/0245650 A1* | 10/2011 | Kerwin | ............. | G01R 33/5635 600/407 |

OTHER PUBLICATIONS

CAAS QCA, The applications and benefits of quantitative coronary angiography, Pie Medical Imaging, pp. 1-5, Apr. 2011.

* cited by examiner

*Primary Examiner* — Alex Liew
(74) *Attorney, Agent, or Firm* — Lempia Summerfield Katz LLC

(57) ABSTRACT

The embodiments relate to a method and device for determining plaque deposits in coronary arteries. According to the method, a coronary angiography radiography image of a subject is obtained using an imaging modality. The obtained radiography image is calibrated for further analysis of the radiography image. Image processing techniques such as thresholding and histogram equalization are applied on the radiography image to extract vessel tree structure for analysis. Further, an inner lumen width and an outer vessel width are computed based on the processed radiography image. Further, a level of plaque deposition is determined based on the inner lumen and outer vessel dimensions. Further, the result based on the analysis is displayed to the user. The result includes the level of plaque deposits within the lumen on the vascular structure and possible risks posed by the plaque deposits to a subject.

15 Claims, 10 Drawing Sheets

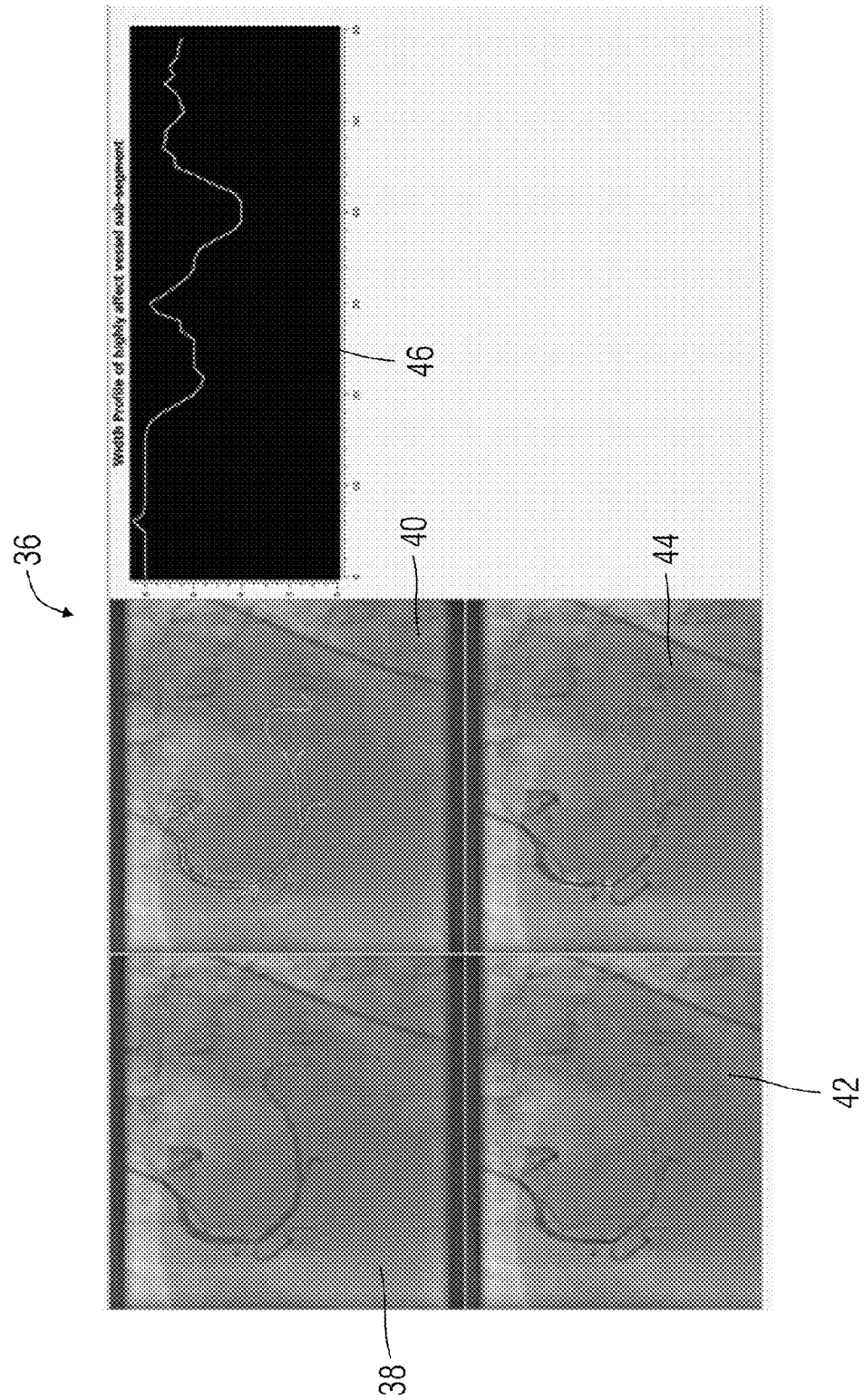

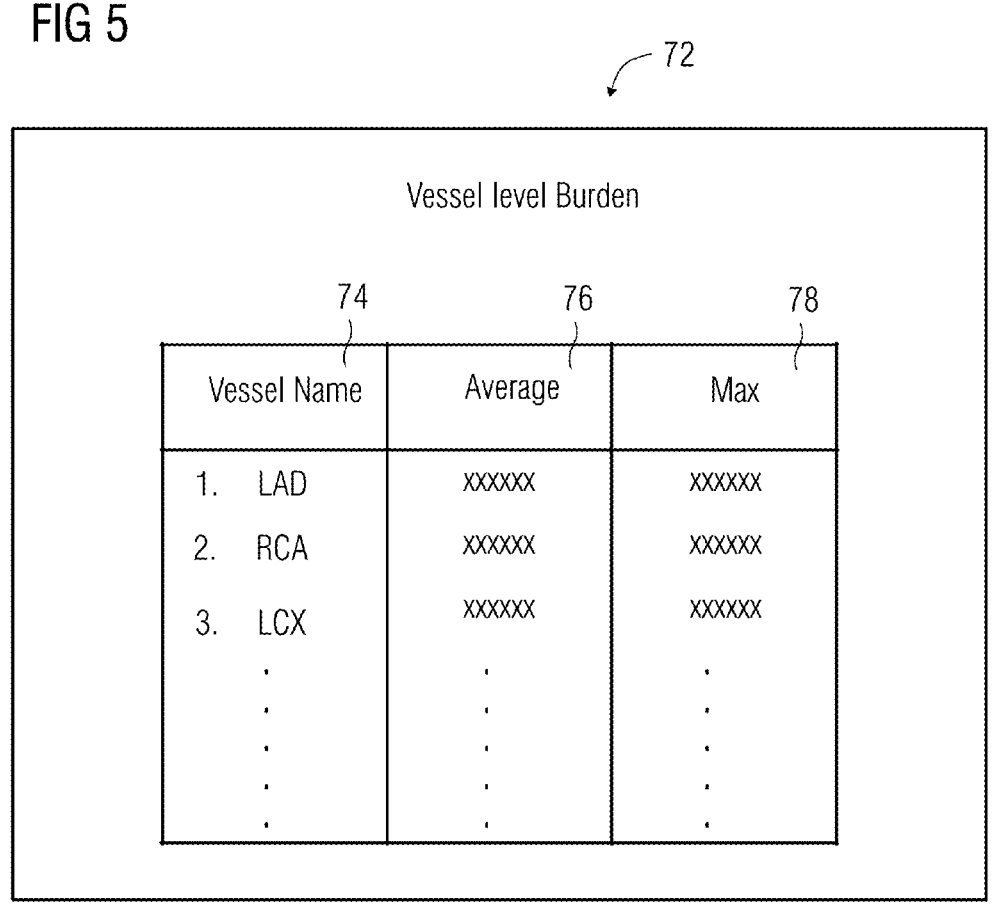

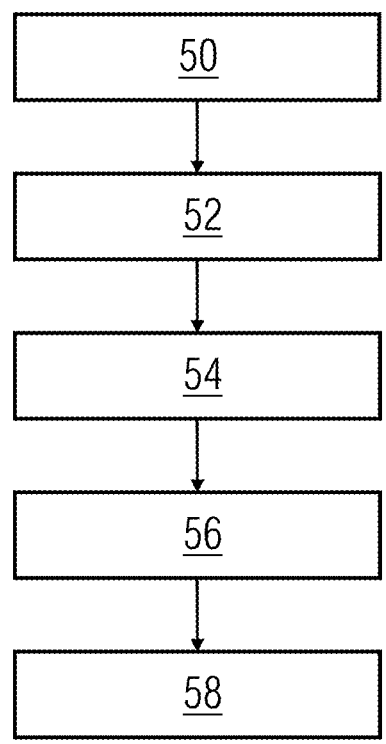

DETERMINING PLAQUE DEPOSITS IN BLOOD VESSELS

TECHNICAL FIELD

The embodiments relate to a method and device for determining plaque deposits in blood vessels. More particularly, the method and device disclosed herein relate to determining plaque deposition in coronary arteries.

BACKGROUND

Atherosclerosis is a common finding in Coronary Artery Disease (CAD) and is a major cause of death and disease world over. Atherosclerosis or plaque/fatty material is deposited in the inner walls of coronary arteries and is widely scattered. An increase in atherosclerosis burden is associated with an increase in adverse events.

In conventional coronary angiography, tools such as Quantitative Coronary Analysis (QCA) are used for quantifying a degree of stenosis in a localized area in a blood vessel. However, there are no tools available that may automatically quantify the atherosclerotic burden in a coronary vascular structure in a diffuse coronary artery disease.

The QCA tool performs a localized analysis of the CAD. The QCA tool is used for analyzing stenosed regions marked by a physician. In other words, a physician marks the Region of Interest (ROI) in a radiography image showing the vasculature of the heart. Further, only the region marked by the physician is analyzed for stenosis. There may be other regions in the vascular structure that may have plaque depositions. Thus, there is a need for a tool that may estimate an overall atherosclerotic burden of an entire coronary vessel tree, which may include branches and crossovers.

Further, the existing tools have known to perform overestimation and underestimation of the plaque deposition in the coronary arteries. For example, there is a case of overestimation in case of calcified plaque deposits and a case of underestimation in the case of soft plaques. This renders the current tools unreliable for estimating an overall atherosclerotic burden. Therefore, there is a need for a tool that reliably estimates the overall atherosclerosis burden.

SUMMARY AND DESCRIPTION

The scope of the present invention is defined solely by the appended claims and is not affected to any degree by the statements within this summary. The present embodiments may obviate one or more of the drawbacks or limitations in the related art.

Accordingly, it is an object of the embodiments to provide a method and device for analyzing plaque deposition in a vascular network, wherein the vascular structure includes a network of blood vessels having at least one of a branch and a crossover and wherein the blood vessels of the vascular structure includes an inner lumen and an outer vessel. The device includes a processor and a memory coupled to the processor, wherein the memory includes a Diffused Coronary Artery Disease (DCAD) estimation module that includes a selection module configured to determine at least two points in a radiography image, wherein the radiography image includes the vascular network of a subject. The DCAD estimation module includes an image enhancement module configured to process the radiography image to enhance the vascular structure between the selected points. The DCAD estimation module further includes a vessel-lumen dimension computation module configured to compute at least a dimension of the outer vessel and a dimension of the inner lumen of the vascular structure between the selected points. The DCAD estimation module includes a plaque deposition determination module configured to determine a level of plaque deposition in the lumen of the vascular structure between the selected points. In some embodiments, the DCAD estimation module estimates the plaque deposition in branches and side vessels of the vascular structure between the selected points.

In accordance with an embodiment, the image enhancement module is configured to apply one or more image processing algorithms to enhance the vascular structure in the radiography image. Image processing algorithms may include Contrast limited adaptive histogram equalization and coherence based anisotropic diffusion. The algorithms improve the contrast of the radiography image by dividing the radiography image into a plurality of blocks. The contrast of each block of the plurality of blocks of the radiography image is enhanced by remapping histogram intensities to a wider dynamic range.

In accordance with another embodiment, the vessel-lumen dimension computation module is configured to compute the inner lumen dimension of the vascular structure using a centerline detection algorithm. The centerline detection of the vascular structure is determined using an edge detection algorithm.

In accordance with yet another embodiment, the vessel-lumen dimension computation module is configured to compute the outer vessel dimension in small segments. The outer vessel dimension is computed by considering tapering of the blood vessels and plausible plaque deposits. In order to mitigate the tapering effects and plaque deposits, a sufficiently small segment of the blood vessel is considered for computing the outer vessel dimension.

In still yet another embodiment, the plaque deposition determination module is configured to determine a distribution of plaque within the vascular structure by computing the difference between the inner lumen dimension and the outer vessel dimension.

In one aspect, a presentation module is configured to annotate the plaque deposition on the radiography image and display the radiography image. The presentation module may divide a display screen into a plurality of segment and display the original image along with a final image in the segments.

In another aspect, the radiography image is a coronary angiography image. The radiography image may be obtained by using X-ray based techniques such as fluoroscopy.

In certain embodiments, a method is provided for analyzing plaque deposition in blood vessels. The method includes an act of selecting at least 2 points in a radiography image of a vascular structure. Subsequently, a vessel tree of the vascular structure is extracted within the selected points of the radiography image. Thereafter, a dimension of inner lumen dimension and an outer vessel dimension of the vessel tree is determined. Further, an extent of plaque deposition based on the inner lumen dimension and outer vessel dimension is determined. Further, the extent of plaque deposition in the vessel tree is displayed.

In one aspect, the act of extracting a vessel tree includes at least one of computation of a Hessian matrix and applying a segmentation algorithm on the radiography image. The vessel tree may be extracted from the radiography image by applying a histogram equalization techniques and coherence based techniques. The radiography image is smoothened to improve the Gaussian fit. Further, the coherence based anisotropic diffusion is applied to eliminate the artefacts in the radiography image due to the application of histogram equalization. Thereafter, to further enhance the vessel tree the Hessian matrix of the vessel tree is computed. The Hessian matrix is computed using a second derivative of a Gaussian kernel. Traditional Gaussian filters when used as a kernel for a given scale, the kernel size increases linearly based on the given scale. To counter adverse effects due to the linearity, a scale adaptive non-linear function is applied. In an embodiment, a scale adaptive trimmed Gaussian kernel is applied. The non-linearity is between the scale and the kernel width at which the kernel is trimmed. The kernel width is not trimmed on the basis of the standard deviation of the distribution but configured to the possible scales of the vessel. For a given set of scales $\sigma=\{\sigma_1, \sigma_2, \ldots \sigma_N\}$, the trimmed Gaussian kernel is given as below in equation 1:

$$Hw = \#\left\{e^{\frac{x^2}{2\sigma^2}}\right\} > T \quad (1)$$

$$\forall x \in \{1:N\}_{N=6\sigma_N}$$

where $T = K\ e^{ax}$, where a and K are constants.

In another aspect, the act of determination of the inner lumen dimension includes determination of a centerline of the vessel tree. The centerline of the vessel tree may be determined using, for example, a combination of mean curvature motion technique and Mumford-Shah model.

In yet another aspect, the inner lumen detection includes computing a distance transform on one or more points on the centerline of the vessel tree.

In yet another aspect, the determination of outer vessel dimension includes dividing the vessel tree into one or more segments, wherein the segment size varies based on a variation of inner lumen dimension. The inner lumen dimension is computed based on the processed radiography image. A variation in the inner lumen dimension indicates a potential plaque deposition in the blood vessel. Therefore, the size of the segment used for computing the outer vessel dimension is changed based on the variation of the inner lumen dimension.

In still yet another aspect, the determination of outer vessel dimension includes using the centerline of the vascular structure and computing a median of an outer dimension of a segment of a blood vessel of the vessel tree. The length of the segment for which the width is calculated is determined by considering tapering effects and possible plaque deposits.

In yet another aspect, determining an extent of plaque deposition includes computing a difference between the inner lumen dimension and the outer vessel dimension. The extent of plaque deposition or the diffused Coronary Artery Disease (CAD) is determined and annotated over the radiographic image.

In yet another aspect, displaying the extent of plaque deposition on the radiography image includes displaying an artery level plaque deposition and a view level plaque deposition.

BRIEF DESCRIPTION OF THE DRAWINGS

FIG. 2I illustrates an exemplary radiography image annotated with an overall estimate of plaque deposition in the blood vessel, in accordance with an embodiment.

FIG. 3 illustrates an exemplary user interface for presenting the radiography images that depicts the overall plaque burden in the vascular structure of the radiography image, in accordance with an embodiment.

FIG. 5 illustrates an exemplary interface for presenting artery level burden, in accordance with an embodiment.

FIG. 6 illustrates exemplary method acts involved in determining plaque deposits in blood vessels, in accordance with an embodiment.

Figure 1:
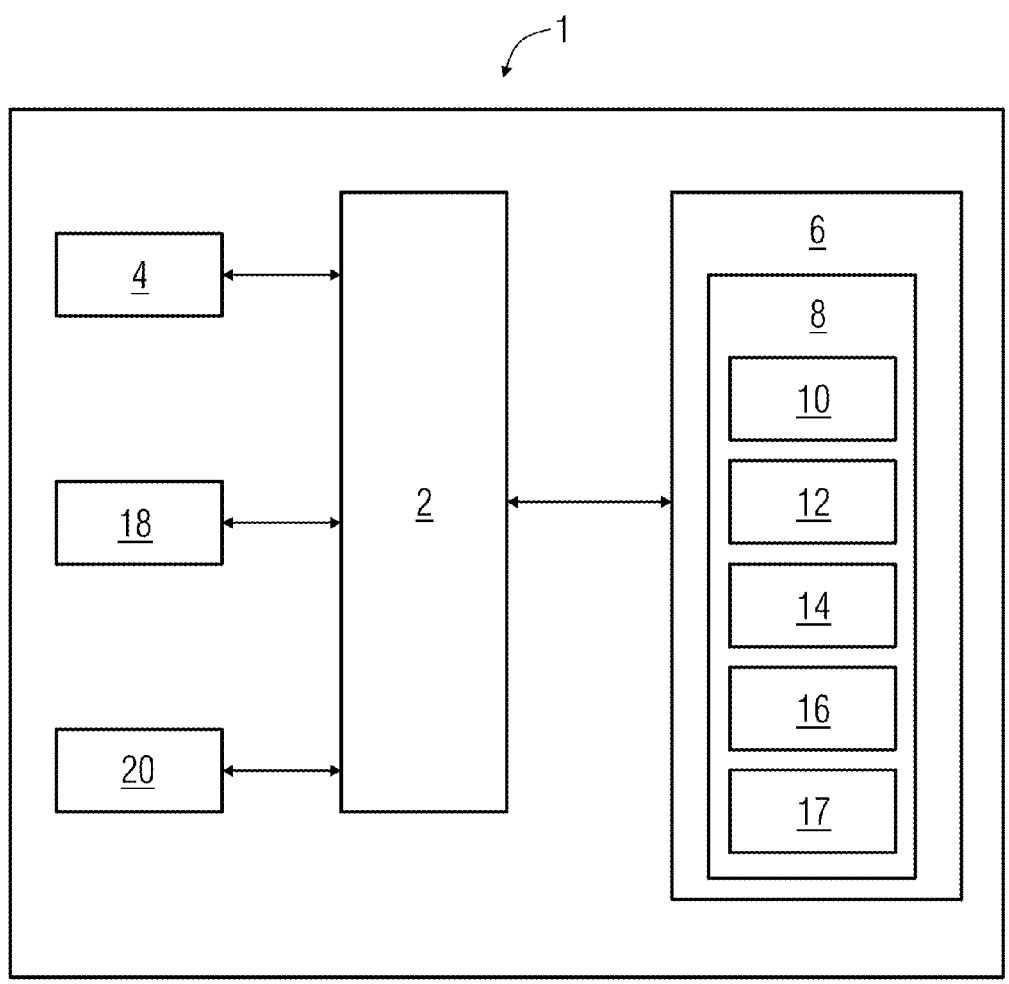
FIG. 1 illustrates a block diagram of an exemplary device for determining plaque deposits in blood vessels, in accordance with an embodiment.

Various embodiments are described with reference to the drawings, wherein like reference numerals are used to refer like elements throughout. In the following description, for the purpose of explanation, numerous specific details are set forth in order to provide thorough understanding of one or more embodiments. It may be evident that such embodiments may be practiced without these specific details.

DETAILED DESCRIPTION

FIG. 1 illustrates a block diagram of an exemplary computing device for determining plaque deposits in blood vessels, in accordance with an embodiment. The computing device 1 may be a personal computer, a laptop computer, a server computer, a tablet and the like. In FIG. 1, the computing device 1 includes a processor 4, a memory 6, a storage unit 18, and input/output devices 20.

The processor 4, as used herein, refers to any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of processing circuit. The processor 4 may also include embedded controllers, such as generic or programmable logic devices or arrays, application specific integrated circuits, single-chip computers, and the like.

The memory 6 may be volatile memory and non-volatile memory. A variety of computer-readable storage media may be stored in and accessed from the memory 6. The memory 6 may include any suitable elements for storing data and machine-readable instructions, such as read only memory, random access memory, erasable programmable read only memory, electrically erasable programmable read only memory, hard drive, removable media drive for handling compact disks, digital video disks, diskettes, magnetic tape cartridges, memory cards, and the like. As depicted, the memory 6 includes a Diffused Coronary Artery Disease (DCAD) estimation module 8 for estimating the extent of plaque deposition in cardiac blood vessels, according to one or more embodiments described above.

The DCAD estimation module 8 is configured to estimate an overall distribution of plaque deposits within the coronary arteries. The DCAD estimation module 8 performs one or more image processing operations on a radiography image of a coronary vascular structure and estimates the distribution of the plaque in the coronary artery. In an exemplary embodiment, the DCAD estimation module 8 selects an appropriate radiography image for processing from one or more radiography images using. The one or more radiography images are obtained by at least one of, capturing the radiography images from an imaging modality or fetching the radiography images stored in a database. The DCAD estimation module 8 includes is configured to select the appropriate frame by applying frame selection algorithms such as contrast frame detection algorithm.

After the selection of the radiography image for further processing, the DCAD estimation module generates a user interface for enabling a user to select a plurality of points on the vascular structure in the radiography image. Once the user selects the plurality points in the radiography image, the DCAD module estimates the extent of distribution of plaque within the selected points of the vascular structure.

The DCAD estimation module 8 includes a selection module 10, an image enhancement module 12, a vessel-lumen dimension computation module 14, and a plaque deposition determination module 16. The selection module 10 is configured to determine at least two points in the vascular structure of the radiography image. The 2 points may include a proximal point (P) and a distal point (D). The DCAD estimation module 8 computes the plaque distribution within the selected points. The selection module 10 may determine the points based on a user selection. The selection module 10 generates a graphical user interface for enabling the user to select a plurality of points on the radiography image. Further, the user may use one or more input devices such as a mouse or a touch interface to select the points on the radiography image. A vessel tree between the selected points is then analyzed for estimating the plaque deposition.

In an exemplary embodiment, the DCAD estimation module 8 includes the image enhancement module 12, which is configured to enhance the visibility of the vascular structure in the radiography image. The image enhancement module 12 is configured to apply one or more image enhancing algorithms on the radiography image. In an embodiment, the image enhancement module 12 applies a contrast limited adaptive histogram equalization algorithm in a first stage, which improves a contrast of the image and segments the image into one or more blocks. Further, the contrast of each block of the radiography image is enhanced by remapping local intensity histograms to a wider dynamic range. The application of the aforementioned algorithm improves a vessel to background ratio. Furthermore, the image enhancement module 12 applies a coherence based anisotropic diffusion algorithm on the radiography image to further enhance the vascular structure. The coherence based anisotropic diffusion algorithm uses a heat equation for removing noise due to the histogram equalization. The coherence based anisotropic diffusion algorithm smoothens in the direction of the vessels so as to improve the image enhancement performance. The coherence based anisotropic diffusion algorithm is used along with hessian methods to render a smoother vessel enhanced radiography image.

In another embodiment, the image enhancement module 12 applies one or more vessel enhancement algorithms on the radiographic image. In an embodiment, the image enhancement module 12 may apply vesselness measures based on Eigen system of the Hessian matrix. The Eigen vectors and Eigen values of the Hessian matrix are used to enhance the curvilinear profiles of the blood vessels, using normalized scale space derivatives. In an embodiment, a second derivative of the Gaussian kernel is used to compute the Hessian matrix. The second derivative of the Gaussian kernel acts as a probe to measure a contrast between the structures and the background to enhance the vascular structure.

In an embodiment, the DCAD estimating module includes the vessel-lumen dimension computation module 14 configured to compute at least a dimension of the outer vessel and a dimension of the inner lumen of a vessel tree between the selected points. The vessel tree may be a part of the vascular structure that is between the user selected points on the vascular structure. In an embodiment, the vessel lumen dimension computation module 14 computes the width of the inner lumen and a width of the outer vessel of the vessel tree. The vessel-lumen dimension computation module 14 may perform segmentation of the vessel tree using a combination of mean curvature motion techniques and Mumford-Shah Models. The segmentation is performed with a requirement of user interference. Thereafter, the vessel-lumen dimension computation module 14 computes a centerline by applying a centerline detection algorithm on the enhanced vessel tree between the selected points.

Thereafter, the vessel-lumen dimension computation module 14 detects the inner lumen dimension upon calculating the centerline of the vessel tree. In an embodiment, the vessel-lumen dimension computation module 14 computes the inner lumen width of the vessel tree by computing a distance transform at various points on the centerline. Also, the vessel-lumen dimension computation module 14 computes a distance transform of the segmented vessel tree and determines a minimum distance of every point inside the vessel tree from the boundary, at sub-pixel level accuracy.

Further, the vessel-lumen dimension computation module 14 computes the outer vessel width of the blood vessels. In order to get an accurate outer width, the vessel-lumen dimension computation module 14 computes the outer width of a segment of the blood vessel. The determination of outer vessel dimension includes dividing the vessel tree into one or more segments wherein the segment size varies based on a variation of inner lumen dimension. The inner lumen dimension is computed based on the processed radiography image. A variation in the inner lumen dimension indicates a potential plaque deposition in the blood vessel. Therefore, the size of the segment used for computing the outer vessel dimension is changed based on the variation of the inner lumen dimension. The length of each segment is computed based on the variations in the inner lumen width. For example, for regions in the vessel tree without drastic changes in the lumen width a size of X is chosen. When a discontinuity is determined in the lumen width the size of the chunk is taken as 2X, where length X straddling the stenosis, X/2 on either side of the stenosis. Thereafter, the outer width of the blood vessel is computed empirically for fixed length segments to eliminate the adverse effects of tapering and plaque depositions.

In another embodiment, the DCAD estimation module includes the plaque deposition determination module 16. The plaque deposition determination module 16 is configured to determine a level of plaque deposition in the lumen of the vascular structure between the selected points. The plaque deposition determination module 16 computes the difference between the outer vessel dimension and the inner lumen dimension. Based on the difference, an overall plaque burden on the blood vessels is computed. Additionally, vessel-lumen dimension computation module 14 differentiates between the highly affected areas and unaffected/pristine areas of the blood vessel.

The storage unit 18 may be a non-transitory storage medium configured for storing files and databases. For example, the storage unit 18 contains one or more radiography images that may be retrieved for performing analysis. Further, the radiography images used for plaque deposition analysis may be located at a remote server and may be remotely accessed via a network connection.

The input/output devices 20 may include keyboard, keypad, monitor, touch sensitive display screen, mouse, and the like. The input device/output devices 20 enable the user to select the points on the vascular structure for analysis of atherosclerotic burden. For example, the display screen may display the selected radiography image and the results of the analysis for the deposition of plaque in the blood vessels in a presentable manner.

Figure 2A:
FIG. 2A illustrates an exemplary radiography image used for determining plaque deposits, in accordance with an embodiment.
Figure 2B:
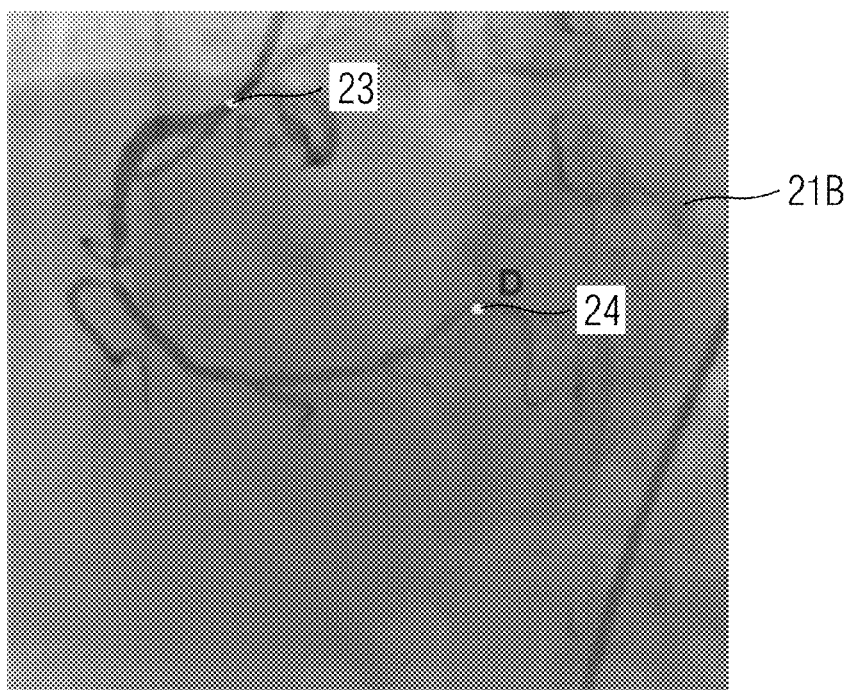
FIG. 2B illustrates an exemplary radiography image after applying image wherein two points in the vascular structure are selected, in accordance with an embodiment.
Figure 2C:
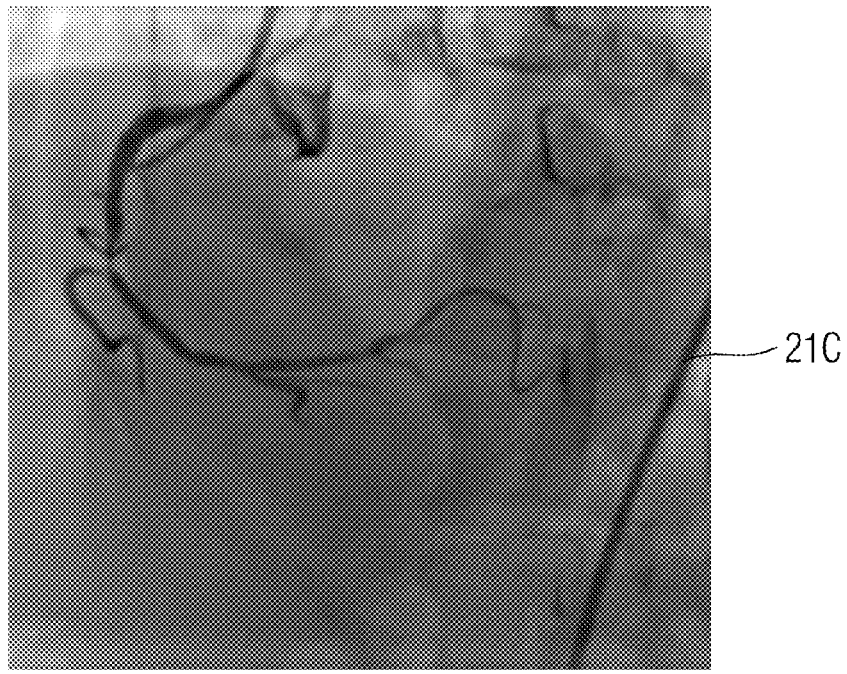
FIG. 2C illustrates an exemplary radiography image with enhanced vascular structure after the application of image enhancement algorithms by the image enhancement module, in accordance with an embodiment.
Figure 2D:
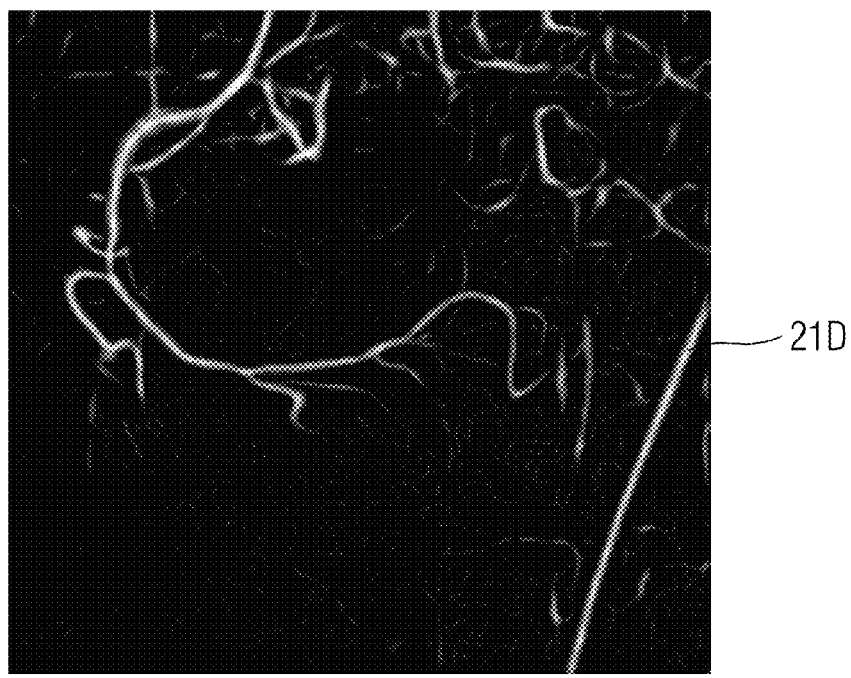
FIG. 2D illustrates another exemplary radiography image with enhanced vascular structure after the application of image enhancement algorithms by the image enhancement module, in accordance with an embodiment.

An exemplary working of the computing device 1 is explained in conjunction with the FIGS. 2A-2I. FIG. 2A illustrates an exemplary radiography image 21A used for determining plaque deposits, in accordance with an embodiment. The radiography image 21A may be extracted from a routine angiography routine or retrieved from a database. The radiography images may be captured with different views of the vascular structure, for example, right anterior oblique (RAO) or Left anterior oblique (LAO). Since the radiography images are 2D images, computing the plaque burden for different views provides an accurate estimate of the overall burden in the blood vessel. Further, image processing acts may be performed in order to select the best radiography image suitable for further processing. For example, frame selection algorithms may be applied to select the best image with required level of contrast, clarity, and brightness. The radiography image 21A is presented to the user using a graphical user interface. FIG. 2B illustrates an exemplary radiography image wherein two points in the vascular structure are selected, in accordance with an embodiment. The user selects the points, 23 and 24, using one or more input devices such as a mouse or a touch interface. The points are selected based on the vessel tree of the vascular structure to be analyzed. Thereafter, the image enhancement module 12 applies one or more image enhancement algorithms for characterizing the vascular structure. FIG. 2C illustrates an exemplary radiography image with enhanced vascular structure after the application of image enhancement algorithms by the image enhancement module, in accordance with an embodiment. In an embodiment, the image enhancement module 12 applies a contrast limited adaptive histogram equalization algorithm on the radiography image 21B thereby generating image 21C. Therein, the image 21C is adaptively broken down into one or more blocks. Thereafter, the vascular structure in the image 21C is modelled to be Gaussian-like in a normal direction. The image may be further enhanced by applying Hessian operators at a later stage. Further, the image enhancement module 12 applies coherence based anisotropic diffusion to further enhance the vascular structure. FIG. 2D illustrates an exemplary radiography image 21D with enhanced vascular structure after the application of image enhancement algorithms by the image enhancement module. It may be apparent to a person skilled in the art that the image 21C is enhanced using any other techniques known in the art.

Figure 2E:
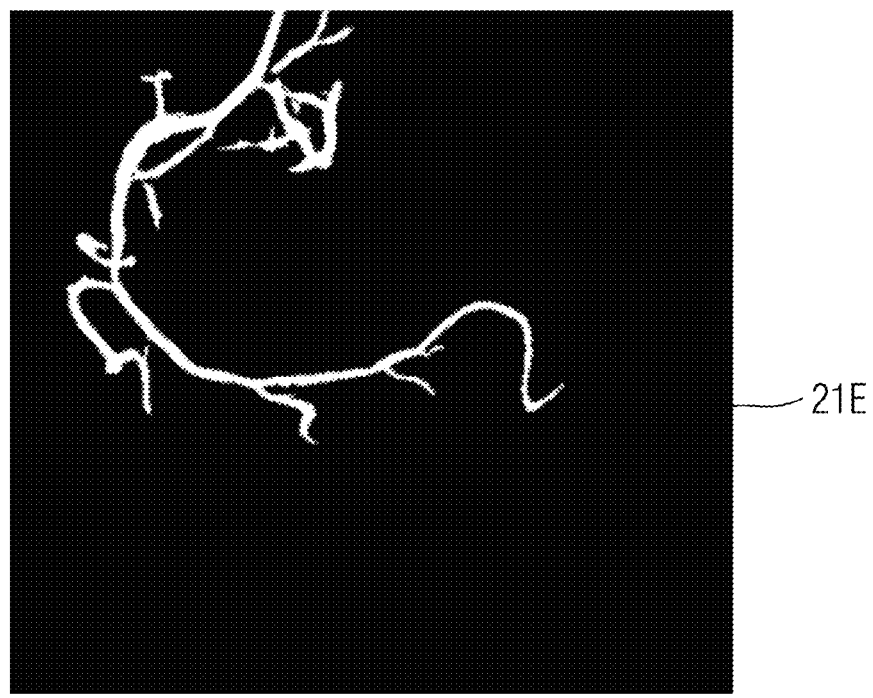
FIG. 2E illustrates an exemplary radiography image after applying segmentation algorithms by the image enhancement module, in accordance with an embodiment.

Further, vessel-lumen dimension determination module 14 applies a segmentation algorithm to the image 21C. FIG. 2E illustrates an exemplary radiography image after applying segmentation algorithm by the vessel-lumen dimension determination module 14. The segmentation algorithm applied by the vessel-lumen dimension determination module 14 is a combination of mean curvature motion techniques and the Mumford-Shah model. The vessel-lumen dimension determination module 14 stops the segmentation algorithm based on an energy minimization equation. The segmentation algorithm is applied on the enhanced radiography image 21C.

Figure 2F:
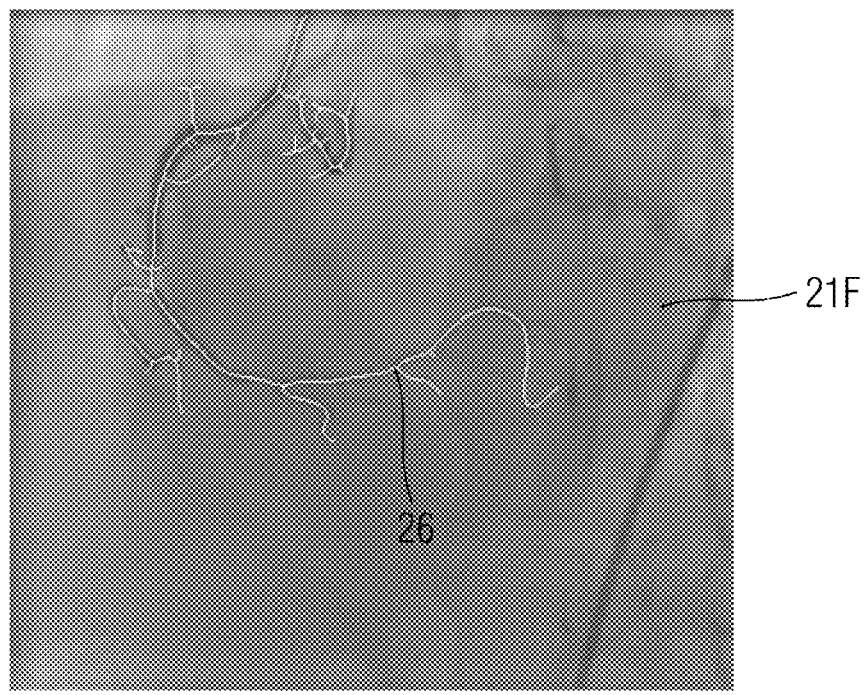
FIG. 2F illustrates an exemplary radiography image after applying a centerline detection algorithm by the vessel-lumen dimension computation module, in accordance with an embodiment.

The vessel-lumen dimension determination module 14 computes the centerline of the vessel tree in the image 21E. FIG. 2F illustrates an exemplary radiography image after applying a centerline detection algorithm by the vessel-lumen dimension computation module 14, in accordance with an embodiment. The pattern 21F is a centerline of the vascular structure in FIG. 2E. The centerline may be computed using methods known in the state of the art, for example, using distance transform method. During the computation of the centerline 26 of the vessel tree, an inner lumen width of the vessel tree is computed.

Figure 2G:
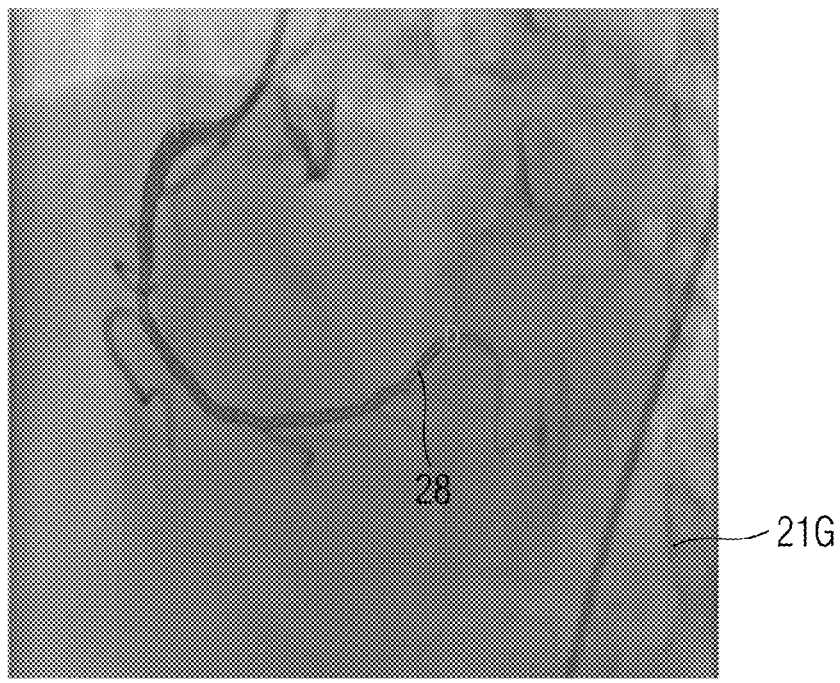
FIG. 2G illustrates an exemplary radiography image annotated with inner lumen width as computed by the vessel-lumen dimension computation module, in accordance with an embodiment.

After computing the centerline 26 of the vascular structure, the vessel-lumen dimension computation module 14 computes the inner lumen width 28 of the portion of the vascular structure between the selected points. The inner lumen width 28 is determined by taking distance transform along the centerline 26 of the portion of the vessel tree. FIG. 2G illustrates an exemplary radiography image annotated with inner lumen width 28 as computed by the vessel-lumen dimension computation module 14, in accordance with an embodiment.

Figure 2H:
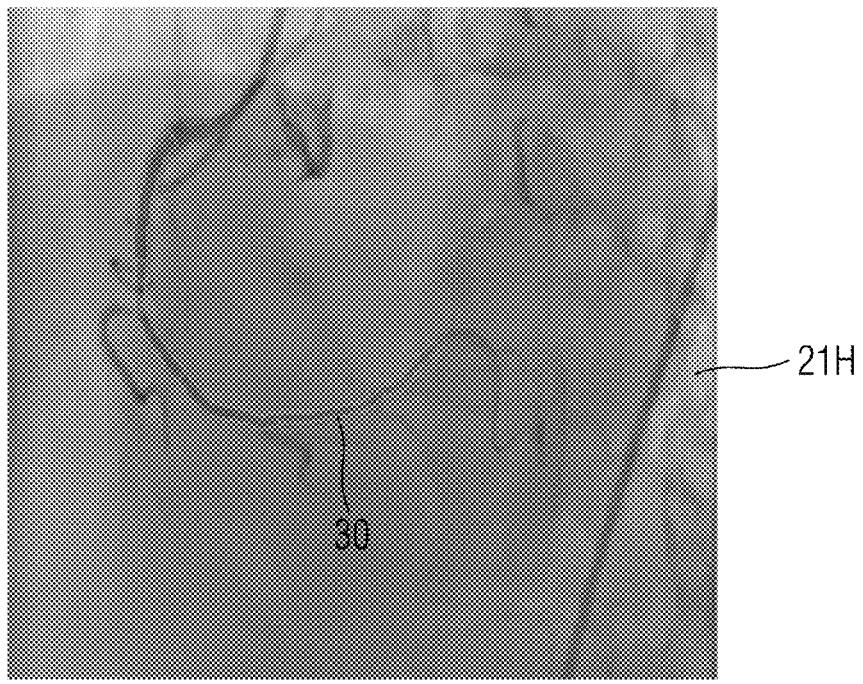
FIG. 2H illustrates an exemplary radiography image annotated with outer vessel width as computed by the vessel-lumen dimension computation module, in accordance with an embodiment.
Figure 21:
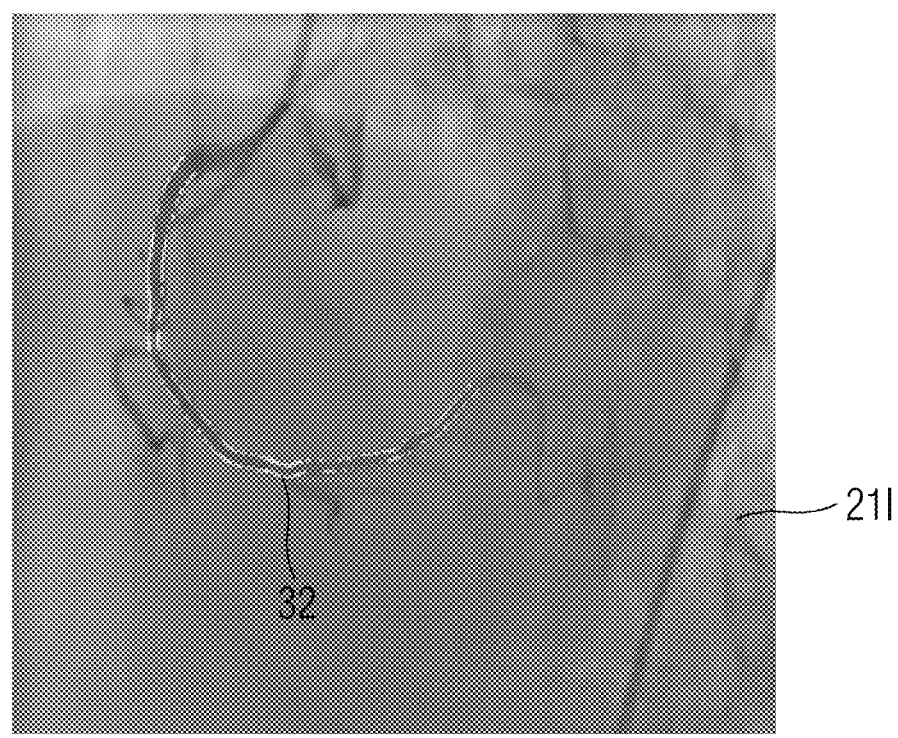

Thereafter, an outer vessel width of the portion of the vascular structure is determined by the vessel-lumen dimension computation module 14. FIG. 2H illustrates an exemplary radiography image annotated with outer vessel width as computed by the vessel-lumen dimension computation module, in accordance with an embodiment. The vessel-lumen dimension computation module 14 computes the outer width by considering segments of the portion of the vascular structure, in order to mitigate the tapering effects and plaque deposits. The segment size for which the outer vessel width is computed is determined so that the outer vessel width 30 is unaffected by tapering effect or the plaque deposits. In one embodiment, a median vessel lumen width of the segment of blood vessel is considered as the outer vessel width 30. Similarly, the outer vessel width is computed by considering all the segments of the portion of the vascular structure. Thereafter, the outer vessel width 30 is annotated over the radiography image and displayed to the user as depicted in FIG. 2H.

Thereafter, the plaque deposition determination module 16 determines the extent of plaque deposition 32 in the blood vessel between the selected points 23 and 24. The extent of plaque deposition 32 is determined by computing a difference between the inner lumen width 28 and the outer vessel width 30. FIG. 2I illustrates an exemplary radiography image annotated with an overall estimate of plaque deposition in the blood vessel, in accordance with an embodiment. It may be observed in FIG. 2I, that the plaque deposition 30 is distributed between the selection points of the vascular structure. In some cases, the thickness of the plaque deposits varies along the path of the blood vessel. The estimation using the disclosed method and device is reliable and accurate as there is less of extrapolation and assumption. Further, the level of plaque deposition may be computed for different views of the vascular structure that provides an accurate estimate of the plaque burden.

Further, the aforementioned modules are configured to estimate the plaque burden using radiography images of different views of the vascular structure, for example, right anterior oblique (RAO) and Left anterior oblique (LAO). In this manner, the accurate estimation of the plaque burden in the vessels is determined. Since plaque deposition is a 3 dimensional object, analyzing it in 2D frame using radiography images may be inefficient. The method and device compute the plaque deposition of the same vessel in different views to enhance accuracy. The more the views of the same vessel, the higher is the accuracy. In an exemplary embodiment, the plaque estimation may be performed at vessel segment level, for example, Proximal, Mid and distal of artery. For example, for a Left Anterior Descending Artery the plaque burden may be calculated for Proximal LAD, Mid LAD and Distal LAD.

FIG. 3 illustrates an exemplary user interface for presenting the radiography images that depicts the overall plaque burden in the vascular structure of the radiography image, in accordance with an embodiment. The user interface includes as plurality of segments, such as segments 38, 40, 42, 44 and 46. In FIG. 3, segments 38, 40, 42 and 44 present the user with various stages of processing the radiography image 21A. For example, segment 38 displays the radiography image where the points 24 and 26 are selected. Segment 40 displays a centerline of the vascular structure. Segment 42 illustrates a lumen width of the portion of the vascular structure. Segment 44 illustrates an overall plaque deposition in the blood vessels of the vascular structure. Further, segment 46 illustrates a width profile of the blood vessel, which also indicates the severity of the blockage of the blood vessel.

Figure 4:
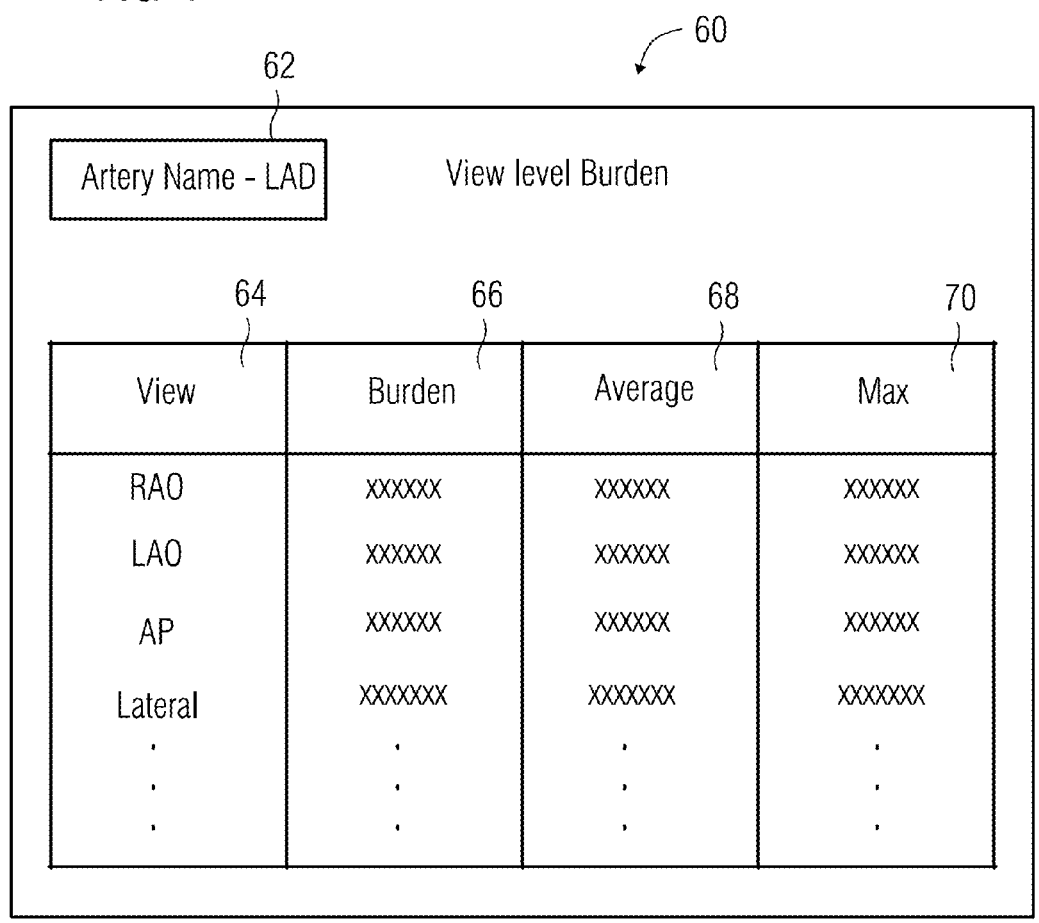
FIG. 4 illustrates an exemplary interface for presenting view level burden of different arteries, in accordance with an embodiment.

FIG. 4 illustrates an exemplary interface 60 for presenting view level burden of different arteries, in accordance with an embodiment. As depicted in FIG. 4, the view level burden displays the plaque burden of different blood vessels at one or more views. For example, for the Left Anterior Descending Artery (LAD) the plaque burden at different view such as right anterior oblique (RAO) and left anterior oblique (LAO) may be presented for determining an overall plaque burden of the coronary circulation. Also, an average plaque burden and a maximum plaque burden are also displayed.

FIG. 5 illustrates an exemplary interface 72 for presenting artery level burden, in accordance with an embodiment. Based on the plaque deposition levels determined, the system displays the plaque burden of different arteries. As depicted in FIG. 5, the plaque burden of different arteries such as Left Anterior Descending Artery (LAD), right coronary artery (RCA) and left circumflex artery (LCX) are displayed to the user. Further, an average value and a maximum value of the plaque burden are also displayed.

FIG. 6 illustrates exemplary method acts involved in determining plaque deposits in blood vessels, in accordance with an embodiment. At act 50, at least two points in a radiography image of a vascular structure are determined. The vascular structure includes a network of blood vessels having at least one of a branch and a crossover. Further, the blood vessels of the vascular structure include an inner lumen and an outer vessel. At act 52, a vessel tree of the vascular structure is extracted within the selected points. The vessel tree is at least a portion of the vascular structure. The vessel tree is enhanced by computing a Hessian matrix and applying a segmentation algorithm based on the Hessian matrix. At act 54, an inner lumen dimension and an outer vessel dimension of the vessel tree is determined. The inner lumen dimension is determined by computing a centerline of the vessel tree. Further, the inner lumen dimension is computed by applying a distance transform on one or more points on the centerline of the vessel tree. The outer vessel dimension is computed by calculating a median of the inner lumen dimension of a segment of a blood vessel of the vessel tree. At act 56, an extent of plaque deposition is determined based on the inner lumen dimension and outer vessel dimension. The extent of plaque deposition is computed by the difference between the inner lumen dimension and the outer vessel dimension. At act 58, the extent of plaque deposition in the blood vessels is displayed. The radiography image may be annotated with plaque deposition information and displayed to the user through a Graphical user interface, such as GUI in FIG. 6.

The method and device disclosed herein provides a robust and accurate estimation of plaque deposits within blood vessels of a vascular structure. The method and device requires minimal user interaction and displays the results in an intuitive manner. Further, the method may be applied over a conventional angiography image and there is no need for additional exposure or radiation. Furthermore, the method and device computes the plaque deposit estimation for different views of the same blood vessel thereby providing an accurate estimation of the plaque burden. The device may be implemented using the existing hardware and does not require special or custom made hardware. The data derived from the method may be used for population based studies to draw inferences on deposition of atherosclerotic plaque in the blood vessels.

While the present invention has been described in detail with reference to certain embodiments, it may be appreciated that the present invention is not limited to those embodiments. In view of the present disclosure, many modifications and variations would be present themselves, to those skilled in the art without departing from the scope of the various embodiments of the present invention, as described herein. The scope of the present invention is, therefore, indicated by the following claims rather than by the foregoing description. All changes, modifications, and variations coming within the meaning and range of equivalency of the claims are to be considered within their scope.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A device for analyzing plaque deposition in a vascular structure, wherein the vascular structure includes a network of blood vessels having at least one of a branch and a crossover, and wherein the blood vessels of the vascular structure comprise an inner lumen and an outer vessel, the device comprising:
   a processor; and
   a memory coupled to the processor, wherein the memory and the processor cause the device to at least perform:
      determining at least two points in a radiography image, wherein the radiography image is a coronary angiography image and comprises the vascular network of a subject;
      processing the radiography image to enhance the vascular structure between the selected points;
      computing at least a dimension of the outer vessel and a dimension of the inner lumen of a vessel tree between the selected points; and
      determining a level of plaque deposition in the lumen of the vascular structure between the selected points, and determine a distribution of plaque within the vascular structure by computing the difference between the inner lumen dimension and the outer vessel dimension.

2. The device in accordance with claim 1, wherein the computed the outer vessel dimension is an outer vessel width of the blood vessels.

3. The device in accordance with claim 1, wherein the processing of the radiography image comprises applying one or more image processing algorithms to characterize the vascular structure from the radiography image.

4. The device in accordance with claim 3, wherein the computed the outer vessel dimension is an outer vessel width of the blood vessels.

5. The device in accordance with claim 1, wherein the inner lumen dimension of the vascular structure is computed using a centerline detection algorithm.

6. The device in accordance with claim 5, wherein the computed outer vessel dimension is an outer vessel width of the blood vessels.

7. The device in accordance with claim 1, wherein the memory and the processor are configured to cause the device to further perform: displaying the plaque deposition of the vascular structure, wherein the presentation module is configured to display an artery level plaque deposition and a view level plaque deposition.

8. A method for analyzing plaque deposition in a vascular structure, the method comprising:
   determining at least two points in a coronary angiography image of a vascular structure, wherein the vascular structure comprises a network of blood vessels having at least one of a branch and a crossover and wherein the blood vessels of the vascular structure comprise an inner lumen and an outer vessel;
   enhancing a vessel tree of the vascular structure within the selected points;
   determining an inner lumen dimension and an outer vessel dimension of the vessel tree;
   determining an extent of plaque deposition based on the inner lumen dimension and outer vessel dimension, wherein the determining the extent of plaque deposition comprises computing a difference between the inner lumen dimension and the outer vessel dimension; and
   displaying the extent of plaque deposition in the blood vessels.

9. The method in accordance with claim 8, wherein the inner lumen detection comprises computing a distance transform on one or more points on a centerline of the vessel tree.

10. The method in accordance with claim 8, wherein enhancing the vessel tree comprises computing a Hessian matrix, applying a segmentation algorithm, or computing the Hessian matrix and applying the segmentation algorithm.

11. The method in accordance with claim 8, wherein the determination of the inner lumen dimension comprises determining a centerline of the vessel tree.

12. The method in accordance with claim 11, wherein the inner lumen detection comprises computing a distance transform on one or more points on the centerline of the vessel tree.

13. The method in accordance with claim 8, wherein the determination of outer vessel dimension comprises dividing the vessel tree into one or more segments, wherein the segment size is determined based on a variation of inner lumen dimension.

14. The method in accordance with claim 8, wherein the determination of outer vessel dimension comprises using the centerline of the vascular structure and computing a median of the inner lumen dimension of a segment of a blood vessel of the vascular structure.

15. The method in accordance with claim 8, wherein the displaying the extent of plaque deposition on the coronary angiography image comprises displaying an artery level plaque deposition and a view level plaque deposition.

* * * * *